United States Patent
Tashjian (10) Patent No.: US 8,157,773 B2
(45) Date of Patent: Apr. 17, 2012

(54) METHOD AND SYSTEMS FOR PROVIDING AN INFUSION DEVICE INTERFACE

(75) Inventor: Paul Tashjian, Phoenixville, PA (US)

(73) Assignee: Animas Corporation, West Chester, PA (US)

( * ) Notice: Subject to any disclaimer, the term of this patent is extended or adjusted under 35 U.S.C. 154(b) by 1283 days.

(21) Appl. No.: 11/631,983

(22) PCT Filed: Jul. 21, 2005

(86) PCT No.: PCT/US2005/025931
§ 371 (c)(1),
(2), (4) Date: Jan. 9, 2007

(87) PCT Pub. No.: WO2006/012446
PCT Pub. Date: Feb. 2, 2006

(65) Prior Publication Data
US 2008/0045923 A1    Feb. 21, 2008

Related U.S. Application Data

(60) Provisional application No. 60/589,623, filed on Jul. 21, 2004.

(51) Int. Cl.
*A61M 5/00* (2006.01)
(52) U.S. Cl. ...................................... 604/244; 604/93.01
(58) Field of Classification Search ............... 604/93.01, 604/174, 180, 244–246, 288.01–288.04, 604/167.01–167.06, 513
See application file for complete search history.

(56) References Cited

U.S. PATENT DOCUMENTS

| 4,430,081 | A | * | 2/1984 | Timmermans | 604/256 |
| 6,056,718 | A | | 5/2000 | Funderburk et al. | |
| 6,302,866 | B1 | | 10/2001 | Marggi | |
| 6,572,586 | B1 | * | 6/2003 | Wojcik | 604/165.01 |
| 6,749,589 | B1 | | 6/2004 | Douglas et al. | |
| 2001/0053889 | A1 | | 12/2001 | Marggi et al. | |
| 2002/0161332 | A1 | | 10/2002 | Ramey | |

FOREIGN PATENT DOCUMENTS
WO  02/07804 A1  1/2002

OTHER PUBLICATIONS

Search Report for PCT International Application No. PCT/US05/25931 mailed Mar. 31, 2006.
European Search Report for EP 05 77 5721, date of mailing Mar. 23, 2010.
Search Opinion for EP 05 775 721.3, date of mailing Oct. 5, 2010.

* cited by examiner

Primary Examiner — Theodore Stigell
(74) Attorney, Agent, or Firm — Wayne C. Jaeschke, Jr.

(57) ABSTRACT

An infusion device comprising an infuser base, a cannula and a ferrule. The infuser base having a bore extending therethrough, the bore having distal and proximal ends and defining a shoulder therebetween. The cannula having distal and proximal ends, the proximal end having an inside first diameter. A flange extends radially outward from the cannula proximal end. The cannula is positioned in the bore such that the flange is positioned adjacent the shoulder. The ferrule has an insertion portion, having an outside second diameter which is substantially equal to the first diameter, and a tapered portion extending from the insertion portion. The ferrule is positioned in the bore such that the insertion portion and a portion of the tapered portion are received in the cannula proximal end and the flange is compressed between the shoulder and the tapered portion to define a seal between the cannula and ferrule.

13 Claims, 6 Drawing Sheets

METHOD AND SYSTEMS FOR PROVIDING AN INFUSION DEVICE INTERFACE

This application is a U.S. National Phase Application of PCT International Application No. PCT/US2005/025931, filed Jul. 21, 2005, which claims priority of U.S. Provisional Application No. 60/589,623, filed Jul. 21, 2004.

FIELD OF THE INVENTION

The present invention generally relates to an infusion device. More particularly, the present invention relates to an infusion device, for example, a medical infusion set, that resists damage from a needle and that is better equipped to maintain hermeticity during use.

BACKGROUND OF THE INVENTION

Devices, such as ambulatory external medical devices, may deliver material, such as insulin or medication, into a patient's body through an infusion device that may include tubes, hollow needles, ferrules, or cannulas or combinations of components. Disposable infusion devices require interfaces, for example, between a ferrule and a cannula, that maintain hermeticity during use. In some situations, in conventional systems, the needle may pierce or score portions of the interface which may reduce hermeticity. Furthermore, conventional systems may not maintain sufficient sealing hermeticity during use.

In view of the foregoing, there is a need for an apparatus for providing an improved infusion device. Furthermore, there is a need for providing an infusion device that resists damage from a needle and is better equipped to maintain hermeticity during use.

SUMMARY OF THE INVENTION

Consistent with embodiments of the present invention, systems and methods are disclosed for providing an infusion device.

In at least one aspect of the present invention, the infusion device comprises an infuser base, a cannula and a ferrule. The infuser base has a bore extending therethrough. The bore has distal and proximal ends and includes a shoulder therebetween. The cannula has distal and proximal ends with the proximal end having an inside first diameter. A flange extends radially outward from the cannula proximal end and the cannula is positioned in the bore such that the flange is positioned adjacent the shoulder. The ferrule has an insertion portion, having an outside second diameter which is substantially equal to the first diameter, and a tapered portion extending from the insertion portion with an increasing diameter. The ferrule is positioned in the bore such that the insertion portion and a portion of the tapered portion are received in the cannula proximal end and the flange is compressed between the shoulder and the tapered portion to define a seal between the cannula and ferrule.

It is to be understood that both the foregoing general description and the following detailed description are exemplary and explanatory only, and should not be considered restrictive of the scope of the invention, as described and claimed. Further, features and/or variations may be provided in addition to those set forth herein. For example, embodiments of the invention may be directed to various combinations and sub-combinations of the features described in the detailed description.

BRIEF DESCRIPTION OF THE DRAWINGS

Although the invention is illustrated and described herein with reference to specific embodiments, the invention is not intended to be limited to the details shown. Rather, various modifications may be made in the details within the scope and range of equivalents of the claims and without departing from the invention.

It is emphasized that, according to common practice, the various features of the drawings are not to scale. On the contrary, the dimensions of the various features are arbitrarily expanded or reduced for clarity. Included in the drawing are the following figures.

DETAILED DESCRIPTION OF THE INVENTION

The following detailed description refers to the accompanying drawings. Wherever possible, the same reference numbers are used in the drawings and the following description to refer to the same or similar parts. While a presently desired embodiment and features of the invention are described herein, modifications, adaptations and other implementations are possible, without departing from the spirit and scope of the invention. For example, substitutions, additions or modifications may be made to the components illustrated in the drawings, and the exemplary methods described herein may be modified by substituting, reordering, or adding steps to the disclosed methods. Accordingly, the following detailed description does not limit the invention. Instead, the proper scope of the invention is defined by the appended claims.

Systems and methods consistent with the invention provide an infusion device which can be attached to the skin of a patient, and to which a supply of liquid medicine, e.g., an insulin pump, may be attached via a hub infusion needle or the like. The infusion device includes a robust interface subassembly to maintain hermeticity during use. Moreover, the interface subassembly may be tolerant of close dimensional tolerances. The interface subassembly generally includes a ferrule and a cannula. The interface subassembly is positionable in an infuser base. The cannula may be configured to free float within the infuser base. The ferrule may comprise a stem, a tapered lead-in, and a cup. The ferrule may be configured to include a proximal seal.

Figure 1:
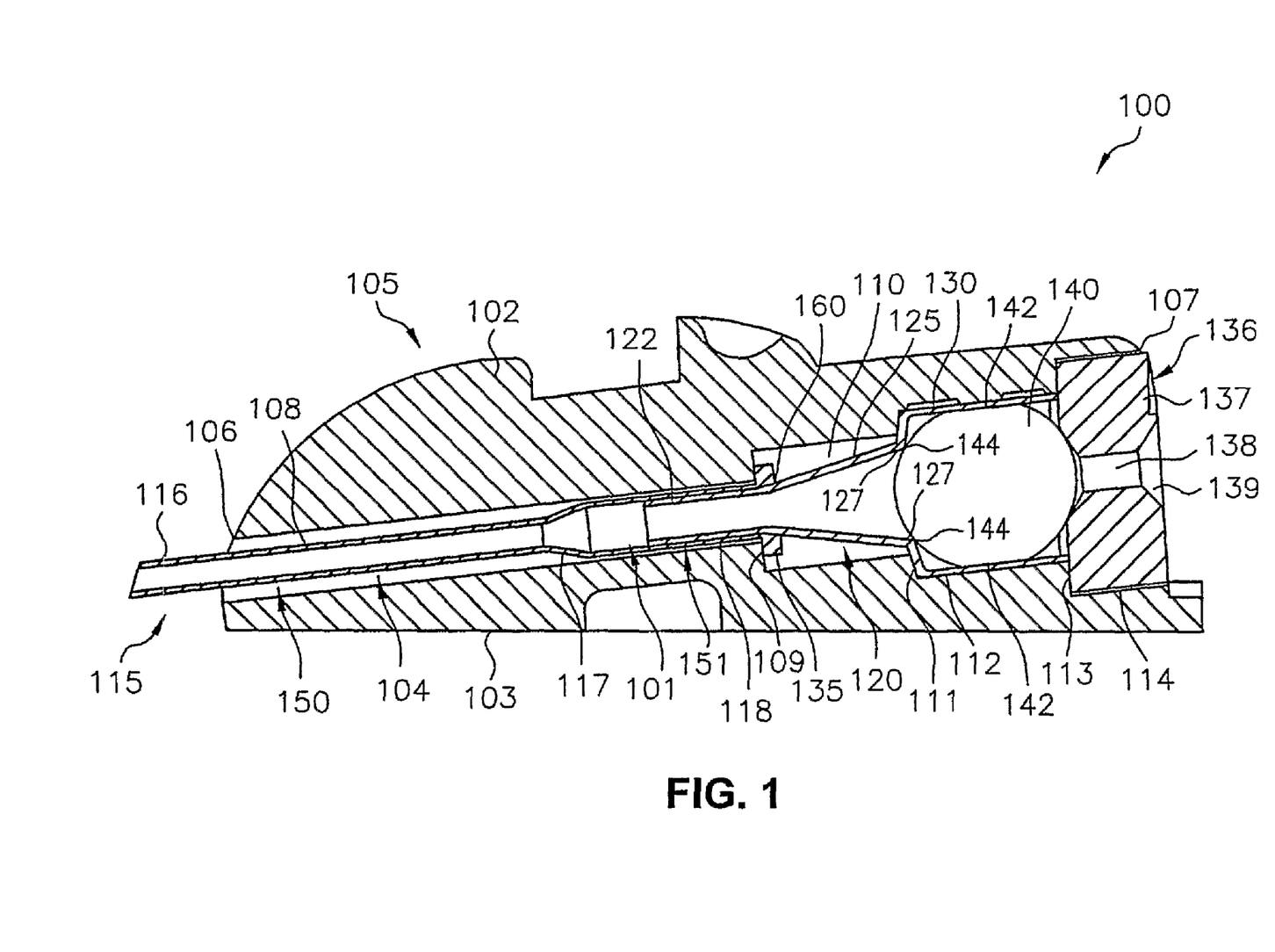
FIG. 1 is a cross-sectional view of an infusion device that is a first embodiment of the present invention.

By way of a non-limiting example, FIG. 1 illustrates infusion device 100 in which the features and principles of the present invention are implemented. As shown in FIG. 1, infusion device 100 generally includes infuser base or housing 105 and interface subassembly 101. Interface subassembly 101 generally comprises cannula 115 and ferrule 120. Infusion device 100 may further include septum 140 and retainer 136.

Figure 2:
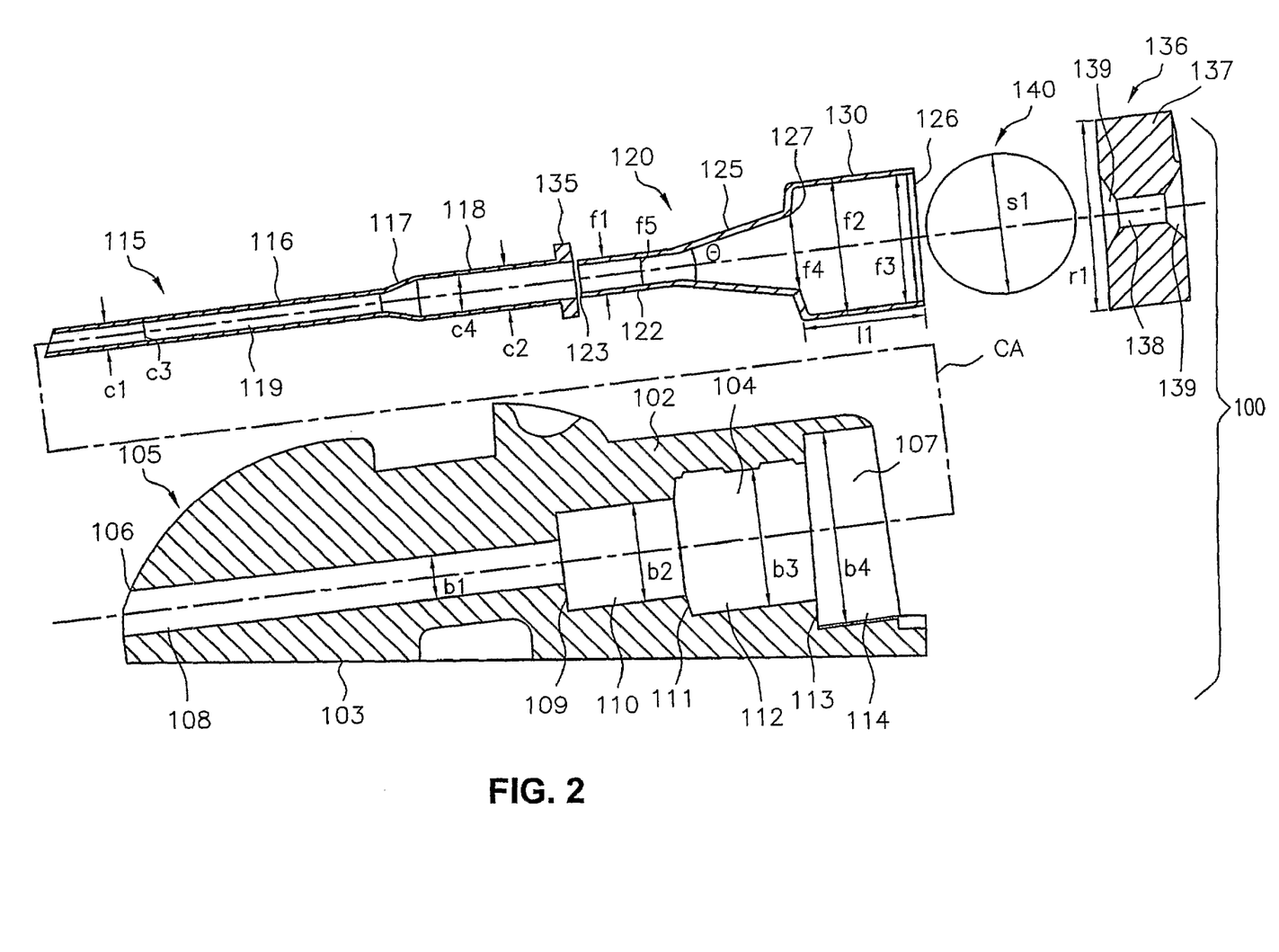
FIG. 2 is an exploded view of the infusion device of FIG. 1.
Figure 6:
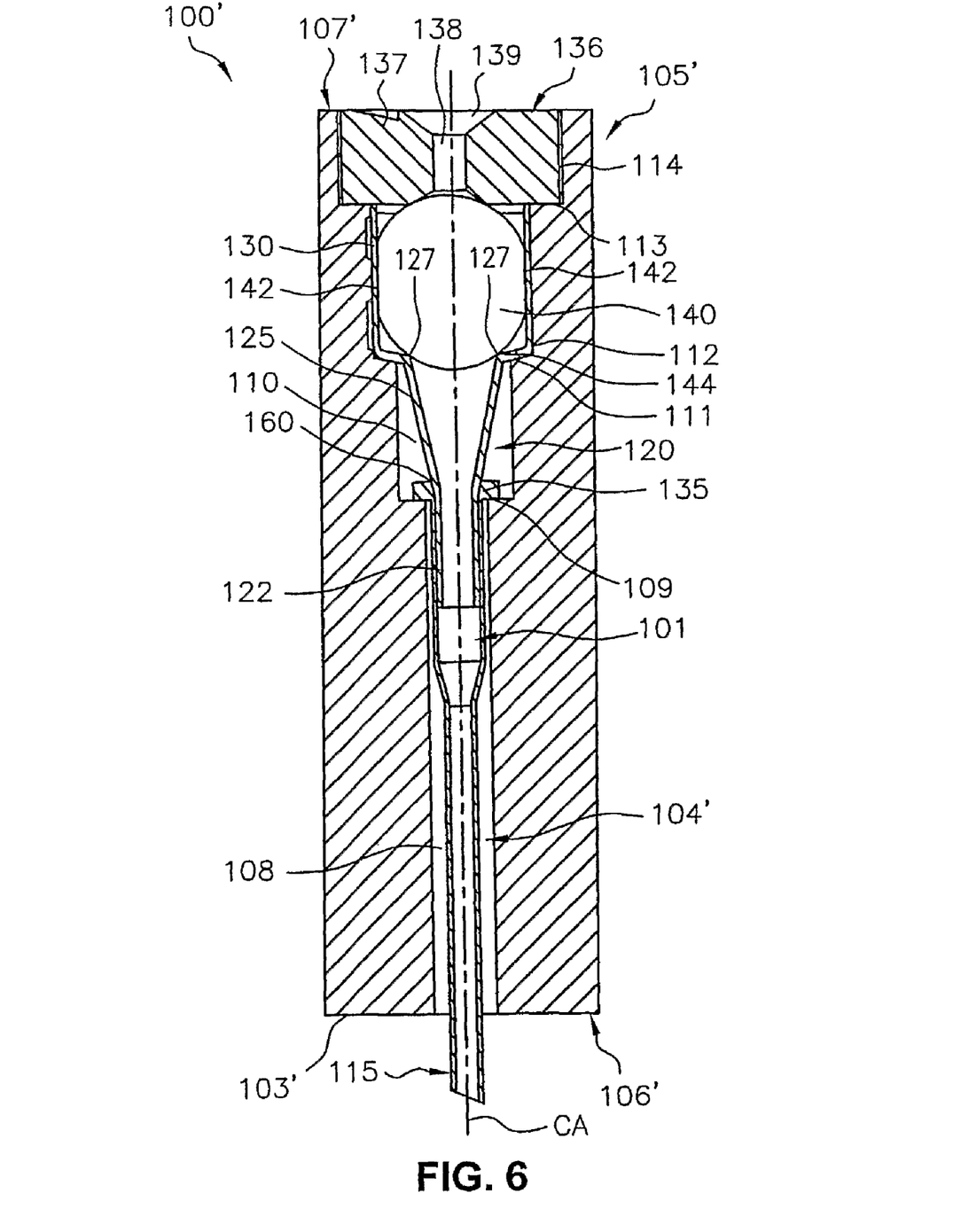
FIG. 6 is a cross-sectional view of an infusion device that is an alternative embodiment of the present invention.

Referring to FIG. 2, the components of the infusion device will be described. Infuser base 105 includes body 102 having base surface 103 configured for position against or proximate an infusion site on a patient. The infuser base 105 may have an adhesive pad (not shown) or the like attached to base surface 103. Bore 104 extends through body 102 between distal end 106 and proximate end 107. Infuser base 105 may have various configurations. For example, the present embodiment illustrates infuser base 105 configured for an angled insertion device with the central axis CA of bore 104 extending at an acute angle relative to base surface 103. Infuser base 105 may have other configurations. For example, infusion device 100' illustrated in FIG. 6 includes infuser body 102' having bore 104' extending between proximal end 107' and distal end 106'. Bore 104' has a central axis CA that extends perpendicular to base surface 103' to provide a straight infusion device. Infusion device 100' otherwise generally operates in a manner similar to infusion device 100 as described herein.

Bore 104 may include differing diameters between distal end 106 and proximal end 107. For example, bore 104 of the present embodiment includes distal portion 108 having the smallest diameter b1 and proximal portion 114 having the largest diameter b4. A pair of intermediate portions 110 and 112 having intermediate diameters b2 and b3, respectively, are provided between distal and proximal portions 108 and 114. Shoulder 109 is defined between distal portion 108 and intermediate portion 110. Shoulder 111 is defined between intermediate portions 110 and 112. Shoulder 113 is defined between intermediate portion 112 and distal portion 114. Bore 104 may have other sizing arrangements. Furthermore, while bore 104 of the present embodiment is cylindrical, it may have other geometric configurations.

Cannula 115 is typically constructed of a medical-grade fluorocarbon-based polymer such as PTFE (PolyTetraFluoroEthylene) or other soft plastic material or non-plastic material. Cannula 115 of the present embodiment includes distal portion 116 having an outside diameter c1 and an inside diameter c3 and proximal portion 118 having an outside diameter c2 and an inside diameter c4. Cannula 115 is relatively thin material and therefore there is only a slight difference between the inside and outside diameters c1, c3 and c2, c4. The distal portion 116 diameters c1, c3 are smaller than the respective diameters c2, c4 of proximal portion 118. Tapered portion 117 extends between the distal and proximal portions 116 and 118 to account for the differences in diameter. The narrower distal portion 116 provides less pain and discomfort during insertion of cannula 115 into a patient while the wider proximal portion 118 allows for a wider receiving area for the insertion needle (not shown in the FIG.).

Cannula 115 also includes flange 135 extending radially outwardly from proximal portion 118. Referring to FIGS. 1 and 2, cannula 115 is configured to be positioned in infuser base bore 104 with the cannula distal, tapered and proximal portions 116, 117, 118 generally positioned in distal bore portion 108 and flange 135 in contact with shoulder 109. Cannula distal portion 116 extends out of bore 104 beyond distal end 106 of base 105. The diameter b1 of bore distal portion 108 is larger than the outside diameters c1 and c2 of cannula portions 106 and 108, respectively, such that circumferential gap 150 (see FIG. 1) is defined about cannula distal and tapered portions 116 and 117 and circumferential gap 151 (see FIG. 1) is defined about cannula proximal portion 118. The functions of gaps 150 and 151 will be described hereinafter.

Figure 3:
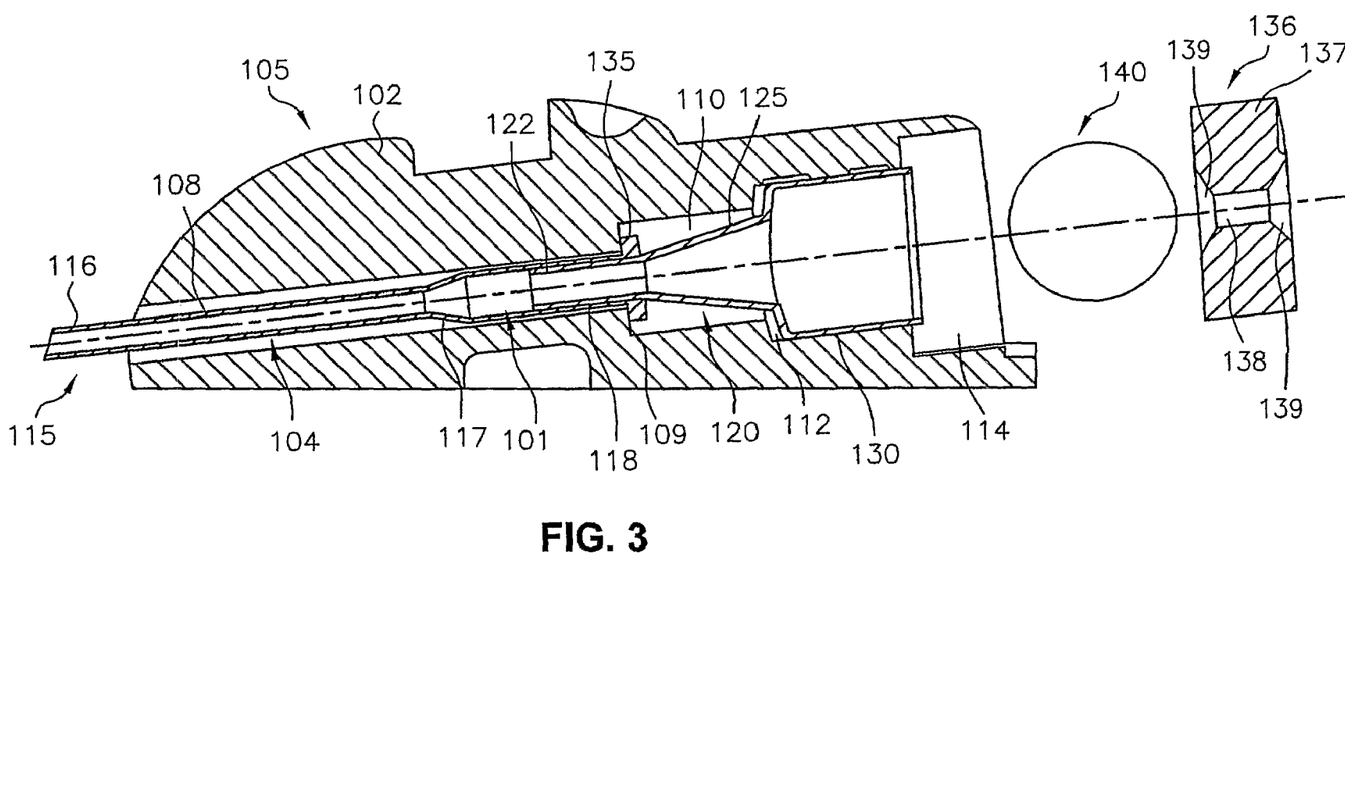
FIG. 3 illustrates the infusion device of FIG. 2 partially assembled.

Referring again to FIG. 2, ferrule 120 has distal end 123 and proximal end 126 and generally includes narrow insertion portion 122 having an outside diameter f1, enlarged proximal portion 130 having an outside diameter f2 and tapered portion 125 therebetween. Ferrule 120 is desirably manufactured from stainless steel or a molded plastic or polymer, but is not limited to such and may be manufactured from various metals and non-metals. The outside diameter f1 of insertion portion 122 is substantially equal to the inside diameter c2 of cannula proximal end 118 such that insertion portion 122 may be received in cannula proximal end 118 with a press fit as shown in FIG. 3. Upon final assembly, see FIG. 1, ferrule 120 is inserted into cannula 115 with a portion of ferrule tapered portion 125 entering cannula proximal end 118, as will be described in more detail hereinafter. The outside diameter f2 of enlarged proximal portion 130 is approximately equal to the inside diameter b3 of bore portion 112 such that enlarged proximal portion 130 is press fit into bore portion 112

Ferrule enlarged proximal portion 130 has an inside diameter f3 and an inside axial length l1. Tapered portion 125 defines circumferential contact surface 127 at the junction with enlarged proximal portion 130. Contact surface 127 has a diameter f4 that is less than the diameter f3. Tapered portion 125 tapers to an inside diameter f5 proximate the insertion portion 122. Tapered portion 125 extends at an angle θ between approximately 20 and 30 degrees, desirably 24 degrees. While tapered portion 125 is illustrated with linear sidewalls, tapered portion 125 is not limited to such. For example, tapered portion 125 may have an axially arcuate configuration, such as a concave or convex arc, or a combination of axially arcuate and axially linear configurations.

Soft elastomeric septum 140 is configured to be positioned in ferrule enlarged proximal portion 130 with an interference fit. Septum 140 desirably has a durometer of between approximately 30 shore A and 80 shore A, but is not limited to such. Septum 140 in the present embodiment is spherical and has a diameter so that is larger than the enlarged proximal portion inside diameter f3 and the enlarged proximal portion axial length l1. As such, when septum 140 is positioned in ferrule enlarged proximal portion 130, as shown in FIG. 1, septum 140 compresses and forms primary circumferential seal 142 along an inside surface of enlarged proximal portion 130 and secondary circumferential seal 144 along circumferential contact surface 127. Both primary and secondary seals 142 and 144 desirably provide specific contact areas that span, for example, 360 degrees. Having dual seal locations desirably provides an advantage over conventional systems by adding double seal redundancy, however, the present invention is not limited to dual seals and may function with only one seal along either the inside surface of enlarged proximal portion 130 or the circumferential contact surface 127. While septum 140 of the present embodiment is spherical, it may have other configurations, for example, barrel or elliptical shapes, complementary to the configuration of ferrule 120 to provide compression contact seals along the inside surface of enlarged proximal portion 130 and/or circumferential contact surface 127. Furthermore, while enlarged proximal portion 130 of the present embodiment has an axial length l1 smaller than septum diameter s1, such is not necessary. Instead, for example, retainer 136, described hereinafter, may be configured with a distally extending portion configured to compress septum 140 toward circumferential contact surface 127.

Retainer 136 of the present embodiment has body 137 with bore 138 therethrough. Body 137 has an outside diameter r1 that is equal to or slightly smaller than the inside diameter b4 of base bore portion 114 such that retainer 136 may be received within base bore 104. In such a configuration, retainer 136 may be sonically welded or otherwise secured to infuser base 105. Alternatively, the diameter r1 may be slightly larger than the diameter b4 such that retainer 136 is press fit into base bore 104. As best shown in FIG. 1, in the installed position, retainer 136 contacts and compresses septum 140 in the distal direction. Retainer 136 may have tapered inlet 139 on at least one side thereof to assist in directing a needle or the like through bore 138. In the present embodiment, tapered inlet 139 is provided on both sides of retainer 136 such that retainer 136 is generally symmetrical, which may prevent it from being installed backwards during the manufacturing process. The invention is not so limited that tapered inlet 139 may be provided on only the inlet side of retainer 136.

Assembly of infusion device 100 of the present invention will be described with reference to FIGS. 1 and 3. Ferrule insertion portion 122 is press fit into cannula proximal end 118 to an extent just before ferrule tapered portion 125 enters cannula 115. Referring to FIG. 3, this integral interface subassembly 101 of cannula 115 and ferrule 120 is positioned into infuser base bore 104 with the cannula distal, tapered and proximal portions 116, 117, 118 generally positioned in distal bore portion 108 and flange 135 in contact with shoulder 109. Cannula distal portion 116 extends out of bore 104 beyond distal end 106 of base 105. While the present embodiment includes interconnection of cannula 115 and ferrule 120 prior to positioning in infuser base bore 104, such is not required. For example, cannula 115 may be positioned in base bore 104 and thereafter ferrule insertion portion 122 inserted into cannula proximal end 118.

Referring again to FIG. 1, robust seal 160 is formed between cannula 115 and ferrule 120 upon fully seating subassembly 101 in infuser base 105. Subassembly 101 is pressed into infuser base bore 104 by forcing ferrule 120 in the distal direction. The distal force causes the under side of flange 135 to contact shoulder 109 in infuser base bore 104. Continued distal force causes ferrule tapered portion 125 to enter cannula proximal portion 118. The increasing diameter of ferrule tapered portion 125 causes flange 135 to expand radially. This expansion creates a tight taper seal 160 between the internal surface of flange 135 and the external surface of flange tapered portion 125. Septum 140 and retainer 136 are positioned as described above with retainer 136 maintaining ferrule 120 in the distally advanced position, thereby maintaining seal 160. The distal force upon ferrule 120 described above may be provided by insertion of retainer 136, or may be otherwise provided, for example, by a removable tool, and thereafter, retainer 136 positioned.

One advantage of this seal 160 over conventional systems is that it generally requires very little radial expansion of flange 135 to create a tight seal. For example, the progressive taper of ferrule tapered portion 122 reduces the need for close tolerances on the axial movement of ferrule 120 relative to flange 135. Accordingly, mating components may be specified with generous tolerances, thus reducing the risk of manufacturing faulty product, for example.

Figure 4:
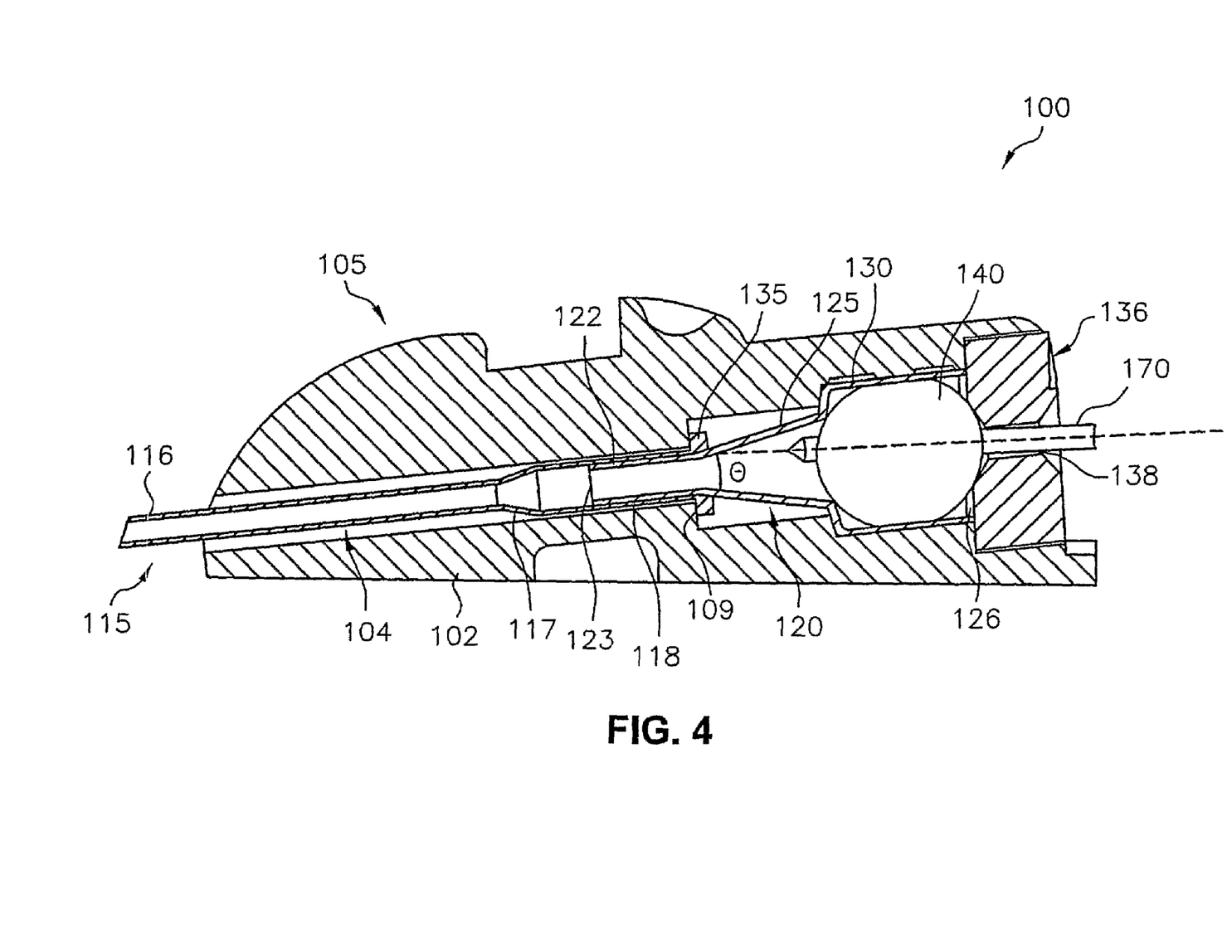
FIG. 4 is a cross-sectional view similar to FIG. 1 showing a misaligned insertion needle partially inserted into the infusion device.

Additional advantages of ferrule tapered portion 122 will be explained with reference to FIGS. 4 and 5. As shown in FIG. 4, if insertion needle 170, configured to be passed completely through cannula 115 and into a patient, is inserted through retainer 136 and septum 140 in a misaligned orientation, i.e., angled relative to cannula 115 centerline, needle 170 will contact tapered portion 125 of ferrule 120. Ferrule tapered portion 125 will generally act to redirect the misaligned insertion needle 170 through distal end 123 of ferrule 120, such that it is again generally coaxial with cannula 115, without damaging or dulling the sharp tip of insertion needle 170. Selecting angle θ, as described above, to comprise a particular value or range of values between 20°-30° and desirably 24°, facilitates the aforementioned redirection of insertion needle 170.

Figure 5:
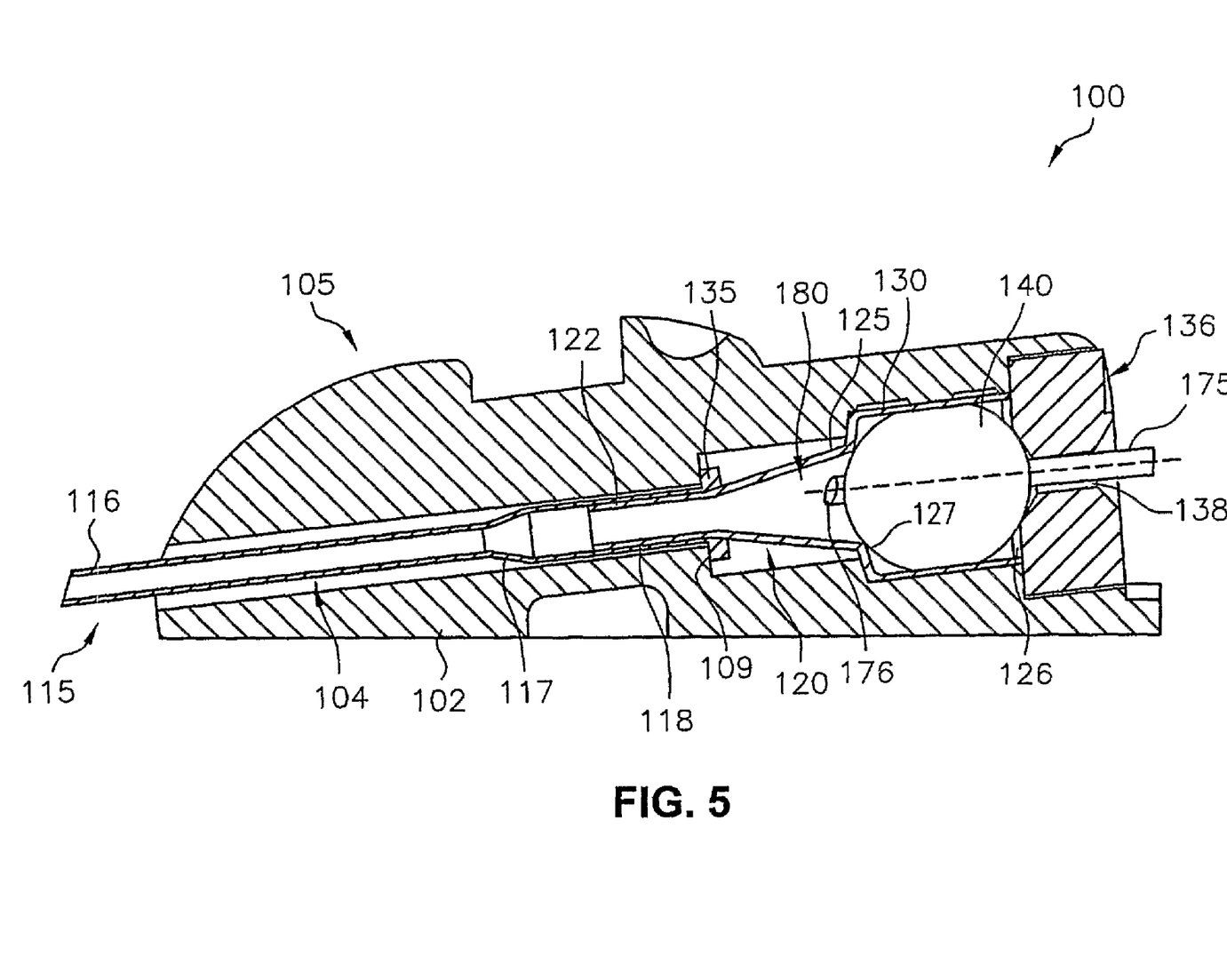
FIG. 5 is a cross-sectional view similar to FIG. 1 showing a hub infusion needle inserted into the infusion device.

Referring to FIG. 5, ferrule tapered portion 125 also provides a free space area 180 for the distal end of infusion hub needle 175. Hub needle 175 is typically attached to an infusion tube or the like and is configured to be passed through septum 140 and retained attached to infusion device 100 to provide a communication path from the infusion tube to the flow path defined by ferrule 120 and cannula 115. Free space area 180 provides a generally open area for distal end 176 of hub needle 175. Free space area 180 generally prevents contact between hub needle distal end 176 and the inner surface of ferrule 120. No contact translates, for example, to minimal connect/disconnect forces of hub needle 175 to infusion device 100. Free space area 180 is defined by circumferential shoulder 127 maintaining septum 140 in place and preventing it from being compressed substantially into ferrule tapered portion 125, which may occur in a conventional assembly.

As explained above with reference to FIGS. 1 and 2, cannula 115 and infuser base bore distal portion 108 are configured such that circumferential gap 150 is defined about cannula distal and tapered portions 116 and 117 and circumferential gap 151 is defined about cannula proximal portion 118. Circumferential gaps 150 and 151 minimize the likelihood that cannula 115 will be damaged. For example, while it is unlikely cannula proximal portion 118 will be contacted by insertion needle 170, circumferential gap 151 provides space for a slightly misaligned interface subassembly 101 from pinching cannula 115 against an internal surface of infuser base 105 during assembly.

Furthermore, as insertion needle 170 is pushed through distal end 123 of ferrule 120, there may be misalignment of the components where the sharp tip or edges of insertion needle 170 may contact the inner surface of cannula tapered portion 117. If there is no space for cannula 115 to deflect from the aforementioned misalignment, the sharp tip and/or edges of insertion needle 170 may cut through or significantly weaken the wall thickness at or distal the inner surface of cannula tapered portion 117, which may induce a leak. Consistent with embodiments of the invention, circumferential gaps 150 and 151 allow cannula 115 to flex about a center axis of infuser base bore 104, thus minimizing the risk of damage or leaks to cannula 115.

While certain features and embodiments of the invention have been described, other embodiments of the invention will be apparent to those skilled in the art from consideration of the specification and practice of the embodiments of the invention disclosed herein. Further, the steps of the disclosed methods may be modified in any manner, including by reordering steps and/or inserting or deleting steps, without departing from the principles of the invention. It is intended, therefore, that the specification be considered as exemplary only, with the true scope and spirit of the invention being indicated by the following claims and their full scope of equivalents. Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An infusion device comprising:
   an infuser base having a bore extending therethrough, the bore having distal and proximal ends and including a shoulder therebetween;
   a cannula having distal and proximal ends, the cannula proximal end having an inside diameter, with a flange extending radially outward from the cannula proximal end, the cannula being positioned in the bore such that the flange is positioned adjacent the shoulder; and a ferrule having a ferrule insertion portion, having an outside diameter which is substantially equal to the cannula proximal end inside diameter, and a ferrule tapered portion extending from the ferrule insertion portion with an increasing outside diameter, the ferrule being positioned in the bore such that the ferrule insertion portion and a portion of the ferrule tapered portion are received in the cannula proximal end and the flange is compressed between the shoulder and the ferrule tapered portion to define a seal between the cannula and ferrule wherein the bore includes a bore distal portion having an inside diameter and wherein the cannula includes:

a cannula distal portion extending in the bore distal portion and having an outside diameter;

a cannula proximal portion extending in the bore distal portion and having an outside diameter, the cannula proximal portion outside diameter being greater than the cannula distal portion outside diameter; and a cannula tapered portion extending between the cannula distal portion and the cannula proximal portion;

wherein the cannula distal portion outside diameter and the cannula proximal portion outside diameter are less than the bore distal portion inside diameter such that at least a first circumferential gap is formed about the cannula distal portion, the cannula tapered portion and the cannula proximal portion.

2. An infusion device comprising:

an infuser base having a bore extending therethrough, the bore having distal and proximal ends and including a shoulder therebetween;

a cannula having distal and proximal ends, the cannula proximal end having an inside diameter, with a flange extending radially outward from the cannula proximal end, the cannula being positioned in the bore such that the flange is positioned adjacent the shoulder; and a ferrule having a ferrule insertion portion, having an outside diameter which is substantially equal to the cannula proximal end inside diameter, and a ferrule tapered portion extending from the ferrule insertion portion with an increasing outside diameter, the ferrule being positioned in the bore such that the ferrule insertion portion and a portion of the ferrule tapered portion are received in the cannula proximal end and the flange is compressed between the shoulder and the ferrule tapered portion to define a seal between the cannula and ferrule, wherein the ferrule includes a ferrule proximal portion extending from the ferrule tapered portion and having an inside surface having a inside diameter, and wherein a circumferential contact surface is defined at a junction between the ferrule tapered portion and the ferrule proximal portion, the circumferential contact surface having an inside diameter that is less than the ferrule proximal portion inside surface diameter, and further comprising an elastomeric septum having an outside radial dimension larger than the ferrule proximal portion inside surface diameter, wherein the elastomeric septum is compressed in the ferrule proximal portion and defines at least a first circumferential seal between the septum and the ferrule proximal portion inside surface or between the septum and the circumferential contact surface.

3. An infusion device according to claim 2 wherein the elastomeric septum further defines a second seal between the other of the ferrule proximal portion inside surface and the circumferential contact surface.

4. An infusion device according to claim 2 wherein the ferrule proximal portion has an axial length that is less than an axial length of the elastomeric septum.

5. An infusion device according to claim 2 wherein the septum is substantially spherical.

6. An infusion device according to claim 2 further comprising a retainer positioned in the bore in contact with the septum to retain the septum in sealing engagement with the circumferential contact surface.

7. An infusion device according to claim 2 wherein the circumferential contact surface is configured to prevent the septum from extending significantly into the ferrule tapered portion such that a free space area is defined within the ferrule tapered portion between an inside surface thereof and the septum.

8. An infusion device comprising:

an infuser base having a bore extending therethrough, the bore having distal and proximal ends;

a cannula positioned in the bore; and a ferrule positioned in the bore and sealingly coupled with the cannula, the ferrule having a distal portion, a proximal portion and a tapered portion therebetween, a junction between the ferrule tapered portion and the ferrule proximal portion defining a circumferential contact surface having an inside diameter that is less than an inside diameter of an inside surface of the ferrule proximal portion; and an elastomeric septum, having an outside radial dimension larger than the inside diameter of the ferrule proximal portion, compressed in the ferrule proximal portion and defining at least a first circumferential seal between the septum and the inside surface of the ferrule proximal portion or between the septum and the circumferential contact surface, wherein the elastomeric septum further defines a second seal between the other of the ferrule proximal portion inside surface and the circumferential contact surface.

9. A method of assembling an infusion device comprising:

providing an infuser base having a bore extending therethrough; the bore having distal and proximal ends and including a shoulder therebetween;

positioning a cannula, having distal and proximal ends and a flange extending radially outward from the cannula proximal end, in the bore such that the flange is positioned adjacent the shoulder;

positioning a ferrule, having a ferrule insertion portion with an outside diameter which is substantially equal to an inside diameter of the cannula proximal end and a ferrule tapered portion extending from the ferrule insertion portion with an increasing outside diameter, in the bore such that the ferrule insertion portion is received in the cannula proximal end; and advancing the ferrule distally such that a portion of the ferrule tapered portion is received in the cannula proximal end and the flange is compressed between the shoulder and the ferrule tapered portion to define a seal between the cannula and ferrule, wherein the ferrule insertion portion is positioned in the cannula proximal end before the cannula and ferrule are positioned in the bore.

10. The method according to claim 9 wherein advancing the ferrule distally includes positioning a retainer in the bore such that the retainer contacts and advances the ferrule.

11. The method according to claim 9 wherein advancing the ferrule distally includes advancing the ferrule with a removable tool and thereafter positioning a retainer in the bore to retain the ferrule in an advanced position.

12. The method according to claim 9 further comprising:

compressing an elastomeric septum in a ferrule proximal portion extending from the ferrule tapered portion and defining an inner surface and a circumferential contact surface at a junction with the tapered surface such that the elastomeric septum defines at least a first circumferential seal between the septum and the inside surface of the ferrule proximal portion or between the septum and the circumferential contact surface.

13. The method according to claim 12 wherein the elastomeric septum further defines a second seal between the other of the ferrule proximal portion inside surface and the circumferential contact surface.

* * * * *